(12) United States Patent
Bergeron et al.

(10) Patent No.: US 6,534,563 B1
(45) Date of Patent: Mar. 18, 2003

(54) USE OF POLYMERS AS STICKING AGENTS

(75) Inventors: Vance Bergeron, Anthony (FR); Jean-Yves Martin, St. Genis les Ollieres (FR); Louis Vovelle, Lyons (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/763,071
(22) PCT Filed: Aug. 17, 1999
(86) PCT No.: PCT/FR99/02002
§ 371 (c)(1), (2), (4) Date: Apr. 6, 2001
(87) PCT Pub. No.: WO00/08926
PCT Pub. Date: Feb. 24, 2000

(30) Foreign Application Priority Data

Aug. 17, 1998 (FR) .............................................. 98 10471

(51) Int. Cl.[7] ................................................. C08K 3/00
(52) U.S. Cl. ......................................... 523/122; 524/27
(58) Field of Search ............................. 524/27; 523/122

(56) References Cited

U.S. PATENT DOCUMENTS

| | | | | | |
|---|---|---|---|---|---|
| 4,013,600 | A | * | 3/1977 | Cassat | 260/174 |
| 4,116,896 | A | * | 9/1978 | Garrett | 260/17 |
| 4,211,681 | A | * | 7/1980 | Braun | 260/29.2 |
| 4,374,738 | A | * | 2/1983 | Kelley | 252/8.5 |
| 5,118,435 | A | * | 6/1992 | Nieh | 252/70 |
| 5,412,007 | A | * | 5/1995 | Hendrix | 524/72 |
| 5,474,712 | A | * | 12/1995 | Dotolo | 252/550 |
| 5,563,186 | A | * | 10/1996 | Thompson | 523/130 |
| 5,985,989 | A | * | 11/1999 | Shawl | 524/755 |
| 6,093,769 | A | * | 7/2000 | Burdick | 524/767 |

* cited by examiner

Primary Examiner—Edward J. Cain

(57) ABSTRACT

The invention concerns the use as sticking agents, in formulations to be used in the presence of an aqueous solution, of at least a compound with elongation viscosity not less than twice that of water and a flow viscosity not more than six times that of water; said viscosity levels being measured for compound concentration levels ranging between 0.05 and 3 g/l.

14 Claims, No Drawings

USE OF POLYMERS AS STICKING AGENTS

This application is an application under 35 U.S.C. Section 371 of International Application Number PCT/FR99/02002 filed on Aug. 17, 1999.

The present invention relates to the use of compounds with particular elongational and flow viscosity characteristics, as an anti-rebound agent included in the composition of formulations used in the presence of an aqueous solution.

More particularly, the present invention relates to the field of plant protection formulations comprising pesticides or agents controlling plant growth.

Further, the present invention relates to plant protection preparations intended for application in the form of a solution, dispersion or emulsion in an aqueous medium to plants to be treated. It should be noted that for simplification, reference will only be made in the description to aqueous solutions, although this term encompasses the variations cited above.

Plant protection formulations used in the presence of an aqueous solution are conventionally sprayed onto the plant to be treated. One of the principal difficulties encountered with this procedure is that it is very difficult to control the quantity of active principle that remains in contact with the plant to be treated. During spraying, a large portion of the active principle is lost as the sprayed droplet rebounds from the hydrophobic surface of the plant and is deposited in an undesirable location (for example the ground). In addition to the economic disadvantage of losing product, depositing an active principle on the earth or indeed on other plants can cause problems with toxicity or phytoxocity.

In order to overcome this problem of undesirable rebound of the droplet of formulation from the surface of the plant to be treated, the introduction of additives has been proposed in order to greatly increase the flow viscosity of the formulation. However, that solution can only be considered to be a partial solution as such formulations are difficult to pump and spray.

There is currently no additive for formulations for use in the presence of an aqueous solution that has both satisfactory flow characteristics as regards the mode of applying that formulation and can avoid the phenomenon of rebound of the droplet of formulation from the surface of the plant to be treated.

The present invention aims to overcome these difficulties.

It consists in the use, as an anti-rebound agent in formulations for use in the presence of an aqueous solution, of at least one compound with an elongational viscosity of twice or more that of water and a flow viscosity less than or equal to six times that of water; these viscosities are measured for compound concentrations in the range 0.05 to 3 g/l.

The compound used as an anti-rebound agent has the dual advantage of eliminating the rebound phenomenon without deleteriously increasing the viscosity of the formulation during its application. In this manner, the formulation is always easy to pump and spray.

Further, said compound endows the solution in which it is used with anti-rebound properties, even when used alone. It is then not necessary to use a surfactant, for example, to obtain good anti-rebound properties.

Further again, the anti-rebound agent of the invention can advantageously be used in a tank-mix, i.e., mixed with the formulation just before its application. The anti-rebound agent of the invention can be present as a biological activator; i.e., it can be formulated with the active principle.

Finally, the anti-rebound agent of the invention can form part of the composition of a number of plant protection formulations that are intended for application in an aqueous medium. Examples that can be cited are solid formulations, in particular wettable powders or dispersible granules; examples of liquid formulations are emulsifiable concentrates, suspensions, suspo-emulsions, and concentrated emulsions.

Further advantages and characteristics will become clear from the following description.

As indicated above, the present invention concerns the use, as an anti-rebound agent in formulations for use in the presence of an aqueous solution, of at least one compound with an elongational viscosity of twice or more that of water and a flow viscosity less than or equal to six times that of water; these viscosities are measured for compound concentrations in the range 0.05 to 3 g/l.

The term "elongational viscosity" means the viscosity measured as a fluid is deformed.

The term "flow viscosity" means the viscosity during simple shear of a fluid.

Further details regarding these viscosities can be obtained from the following work: Rheometry, Chap. VII; K. Walters; Chapman and Hall, 1975, p. 210 ff.

In a particular implementation of the present invention, the compound has an elongational viscosity of ten times or more that of water.

Regarding the flow viscosity of said compound, in a variation of the invention, it is 3 times or less that of water. Preferably, the flow viscosity of the compound is 1.5 times or less that of water.

Advantageously, the compound used as an anti-rebound agent can also have a retraction rate of 200 mm/s or less, preferably 100 mm/s or less.

It should be pointed out that the retraction rate, which corresponds to the phase whereby the diameter of a drop spread on a hydrophobic support reduces, is measured with a formulation comprising 1 g/l of anti-rebound compound, in an aqueous solution. The measurement is carried out by allowing a drop with a diameter of 2 mm to drop from a height of 60 cm onto a hydrophobic surface, i.e., a support for which the contact angle with water is more than 110° (in this case the surface is treated with stearic acid). The variation in diameter of the drop is recorded with a rapid camera capable of taking 1000 photos per second.

The compound used in the invention is selected from hydrosoluble or hydrodispersible surfactant polymers with a molecular weight in the range $5\times10^4$ to $5\times10^6$ g/mol. More particularly, the molecular weight of the compound is in the range $5\times10^5$ to $5\times10^6$ g/mol, preferably in the range $10^6$ to $5\times10^6$ g/mol.

Preferably, the compound used is such that it comprises at least one polymeric chain the molecular weight of which is included in the ranges defined above. Further, this chain is at least 80%, preferably at least 90% soluble in an aqueous medium; the compound is present in a concentration in the range 0.05 to 3 g/l. In a particularly advantageous implementation, the polymeric chain of said compound, and preferably the compound itself, is completely soluble in aqueous media, under the concentration conditions indicated above.

A first category of compound that can be used as the anti-rebound agent is constituted by a polyhydroxylated polymer or copolymer selected from polysaccharides of animal, vegetable or bacterial origin, or from polyvinyl alcohol, polyphenol alcohols, or derivatives thereof.

The polysaccharides can be used in an ionic or non ionic form.

Xanthan gum, succinoglycanes, gum arabic, carragheens and alginates are representatives of anionic polysaccharides; cationic derivatives of starch can also be cited.

Non ionic polysaccharides that can be cited include galactomannans, such as guar gum or its derivatives such as hydroxypropylguar, carouba gum, soluble starch and its non ionic derivatives, cellulose and its carboxyalkylated or hydroxyalkylated derivatives, wherein the alkyl portion contains 1 to 4 carbon atoms.

Polyvinyl alcohol, polyphenyl alcohols or their derivatives are suitable polyhydroxylated polymers or copolymers, as indicated above.

Possible derivatives include polyetherified (co)polymers such as those wherein the ether portion is a $C_1$–$C_{18}$ alkyl radical or a $C_6$–$C_{18}$ aryl radical, or an alkylaryl or arylalkyl radical; the alkyl and aryl portions being as defined above.

Suitable derivatives also include (co) polymers carrying at least one ionic radical (anionic, cationic, zwitterionic, amphoteric). Non limiting examples of anionic radicals are sulphonate type radicals, sulphate, carboxylate, phosphate, phosphonate; examples of cationic radicals that can be cited are quaternary ammonium type radicals such as $N(R)_4^+$ where R, which may be identical or different, represents a hydrogen atom or a $C_1$–$C_6$ alkyl radical; or zwitterionic and amphoteric radicals corresponding to the combination of the two types of radicals cited above.

It should be noted that polyphenyl type (co)polymers are natural substances that can be extracted from certain plants such as coffee and tea plants.

A second advantageous category of possible anti-rebound compound is formed by polyoxyalkyenated derivatives of glycol, the alkylene oxide portion corresponding to ethylene oxide, propylene oxide or mixtures thereof. In the case where ethylene oxide or propylene oxide are present, they may be randomly distributed or in blocks. Preferably, a polyoxyethylenated glycol derivative is used.

Copolymers obtained from an alkylene oxide and at least one saturated or unsaturated monomer comprising one or more carboxyl groups in the form of the acid, alkali metal salt, ester or amide, or comprising an amino or nitrile group, or comprising a heterocyclic group containing nitrogen can also be used.

Examples of saturated or unsaturated monomers containing one or more carboxyl groups that can be cited are $C_3$–$C_{10}$ mono- or di-basic acids, and their derivatives in the form of alkali metal, alkaline-earth metal or ammonium salts (type $N(R)_4^+$ where R represents hydrogen or a $C_1$–$C_6$ alkyl radical), in the form of mono-or di-esters with at least one $C_1$–$C_{12}$ alcohol, more particularly $C_1$–$C_8$, and their N-alkyl derivatives, or in the form of the amide.

Examples that can be cited are acrylic acid, methacrylic acid, itaconic acid, maleic acid, maleic anhydride, fumaric acid, acrylamide, methacrylamide, N-methylolacrylamide, N-methylolmethacrylamide, the salts of the acids or mono- or di-esters obtained from the following acids and alcohols: methanol, ethanol, propanol, n-butanol, isopropanol, isobutanol, 2-ethylhexanol, by way of non-limiting example. Amino acids and their salts or esters such as aspartic acid are suitable for carrying out the invention.

Monomers of the vinyl ester of $C_2$–$C_{10}$ carboxylic acid type, for example vinyl acetate, vinyl versatate or vinyl propionate, are also suitable.

Examples of saturated or unsaturated monomers containing an amino, amido or nitrile group that can be cited include monomers wherein the hydrocarbon chain is $C_3$–$C_{12}$. Examples of saturated monomers that can be cited are acrylonitrile, methacrylonitrile, vinylpyridine, vinylpyrrolidone, vinylimidazole, aminoalkyl (meth) acrylates such as dimethylamino(meth)acrylate, ditertiobutylaminoethyl(meth)acrylate, dimethylamino (meth)acrylamide, ditertiobutylaminoethyl(meth) acrylamide.

A third category of compound that is suitable for use as an anti-rebound agent is constituted by plant polymers such as an alkali metal, alkaline-earth metal or ammonium lignosulphonate.

A fourth category is represented by compounds selected from polymers obtained from at least one saturated or unsaturated monomer, comprising one or more carboxylic groups in the form of an acid, alkali metal salt, ester or an amide, or containing an amino or nitrile group, or comprising a heterocyclic group containing nitrogen, and copolymers obtained by reacting at least one of said monomers with at least one second hydrocarbon-containing monomer carrying one or more ethylenically unsaturated bonds.

Examples of saturated or unsaturated monomers comprising one or more carboxyl groups that can be cited are $C_3$–$C_{10}$ mono- or dibasic acids and their derivatives in the form of alkali metal, alkaline-earth metal or ammonium salts (type $(N(R)_4^+$, where R represents hydrogen or a $C_1$–$C_6$ alkyl radical), in the form of mono- or di-esters with at least one $C_1$–$C_{12}$ alcohol, more particularly $C_1$–$C_8$, and their N-alkylated derivatives, or in the form of an amide.

Examples that can be cited are acrylic acid, methacrylic acid, itaconic acid, maleic acid, maleic anhydride, fumaric acid, acrylamide, methacrylamide, N-methylolacrylamide, N-methylolmethacrylamide, and acid salts or mono- or di-esters obtained from the following acids and alcohols: methanol, ethanol, propanol, n-butanol, isopropanol, isobutanol, 2-ethylhexanol, by way of non-limiting example. Amino acids or their salts or esters, such as aspartic acid, are also suitable.

Monomers of the vinyl ester of $C_2$–$C_{10}$ carboxylic acid type, for example vinyl acetate, vinyl versatate or vinyl propionate, are also suitable.

Examples of saturated or unsaturated monomers containing an amino, amido or nitrile group that can be cited include monomers wherein the hydrocarbon chain is $C_3$–$C_{12}$. Examples of saturated monomers that can be cited are acrylonitrile, methacrylonitrile, vinylpyridine, vinylpyrrolidone, vinylimidazole and aminoalkyl (meth) acrylates such as dimethylamino(meth)acrylate, ditertiobutylaminoethyl(meth)acrylate, dimethylamino (meth)acrylamide and ditertiobutylaminoethyl(meth) acrylamide.

Each of the above monomers can be used in the form of ionic derivatives, i.e., comprising at least one sulphonic function, for example in the acid form or completely or partially in the salt form.

Regarding the second type of monomer, used in combination with those cited above, non limiting examples that can be mentioned are $C_2$–$C_{12}$ hydrocarbons, which may or may not contain an aryl radical, also containing at least one ethylenically unsaturated bond. Suitable examples include butadiene, isobutylene, diisobutylene, styrene, vinylstyrene, alphamethylstyrene, vinyltoluene.

Particularly advantageous polymers that can be cited are polymers such as polyacrylate; polymethacrylate; polyvinylpyrrolidone; polyacrylamide; polyaspartate.

In addition, the following can be mentioned: copolymers of maleic acid or maleic anhydride with isobutylene or diisobutylene; or of pyrrolidone and vinyl acetate.

It should be noted that depending on the nature of the compound used, the aqueous medium can be supplemented, for example, by a base or an acid, such that its pH is adjusted so that the solubility of said compound corresponds to the criteria mentioned above.

The compound used as an anti-rebound agent can be present in the form of a single compound, several compounds forming part of the same category, or several compounds corresponding to several categories.

The anti-rebound compound of the invention can be used in the formulation in two modes.

The first consists of adding it to the formulation during application of the latter (tank-mix additive).

The second consists of adding the anti-rebound compound to the formulation during preparation of the latter (biological activator additive).

Advantageously, the total concentration of the compound in the formulation is in the range 0.05 to 3 g/l. In a more precise variation, said concentration is in the range 0.05 to 1 g/l. Preferably, this concentration is in the range 0.05 to 0.5 g/l.

It should be noted that this concentration range is given for the final formulation, i.e., the formulation that is to be brought into contact with the plant to be treated.

As a result, if the compound is used in a tank mix, then the quantity used is calculated so that the concentration in the final formulation is in the range indicated above.

If the compound is used as a biological activator, then the concentration of this compound in the pre-formulation is calculated as a function of the subsequent dilution of said formulation.

Highly advantageously, the anti-rebound agent of the present invention is used in any plant protection formulation based on active principles of the pesticide type (herbicides, insecticides, fungicides, etc.) or additives for controlling plant growth (oligoelements).

Advantageously, the present invention can be applied to any type of plant protection formulation provided that it is intended to be brought into the presence of a liquid comprising water before being applied to the plants to be treated. In other words, before diluting, the formulations can be in a liquid or solid form.

It should be noted that plant protection formulations are routinely diluted in an aqueous medium before application.

Examples of suitable active principles that can be cited include Ametryne, Diuron, Linuron, Chlortoluon, Isoproturon, Nicosulfuron, Metamitron, Diazinon, Aclonifen, Atrazine, Chlorthalonil, Bromoxynil, Bromoxynil heptanoate, Bromoxynil octanoate, Mancozeb, Manebe, Zineb, Phenmedipham, Propanyl, the phenoxyphenoxy series, the heteroaryloxyphenoxy series, CMPP, MCPA, 2-4-D, Simazine, active principles from the imidazolinone series, the organophosphorated series, in particular Azinphos-ethyl, Azinphos-methyl, Alachlore, Chlorpyriphos, Diclofop-methyl, Fenoxaprop-p-ethyl, Methoxychlore, Cypermethrine, Fenoxycarbe, aminophosphate derivatives, preferably glyphosate, sulphosate, gluphosinate, and their organic salts (ammoniurn salts, which may or may not be substituted, including secondary or primary amines such as isopropylamine, dimethylamine or diamines such as ethylenediamine, or sulphonium salts, in particular trimethylsulphonium) or inorganic compounds (such as salts of alkali metal such as sodium or potassium).

The present invention also relates to the preparation of formulations comprising nutrient elements such as salts of metals such as zinc or iron, preferably manganese, for example. These salts are used in the form of EDTA type chelates, for example, or sulphates.

The constituent elements of plant protection formulations are those generally used in formulations in this field.

Thus, they normally comprise surfactants the role of which can be to stabilise an emulsion, a suspension or a suspo-emulsion, encouraging dispersion of the active principle, and encouraging wetting with other constituents of the formulation.

Said surfactants can be ionic or non ionic.

The quantity of surfactant used depends on the type of formulation. The skilled person would readily be able to determine said quantity.

Non limiting examples of anionic surfactants are:
  alkylsulphonic acids, arylsulphonic acids, possibly substituted with one of more hydrocarbon-containing groups, wherein the acid function is partially or completely in the salt form, such as $C_8$–$C_{50}$ alkylsulphonic acids, more particularly $C_8$–$C_{30}$, preferably $C_{10}$–$C_{22}$, benzenesulphonic acids, naphthalenesulphonic acids, substituted with one to three $C_1$–$C_{30}$ alkyl groups, preferably $C_4$–$C_{16}$, and/or $C_2$–$C_{30}$, preferably $C_4$–$C_{16}$ alkenyl;
  mono- or di-esters of alkylsulphosuccinic acids, wherein the linear or branched alkyl portion may be substituted by one or more linear or branched $C_2$–$C_4$ hydroxyl and/or alkoxyl groups (preferably ethoxylated, propoxylated, ethopropoxylated);
  phosphate esters, more particularly selected from those comprising at least one saturated, unsaturated or aromatic, linear or branched hydrocarbon group containing 8 to 40 carbon atoms, preferably 10 to 30, possibly substituted by at least one alkoxylated group (ethoxylated, propoxylated, ethopropoxylated). Further, they comprise at least one phosphate ester group, mono- or di-esterified such that it is possible to have one or two acid groups that are free or completely or partially in the salt form. Preferred phosphate esters are of the following type: alkoxylated (ethoxylated and/or propoxylated ) mono- or di-esters of phosphoric acid and: mono-, di- or tri-styrylphenol, or mono-, di- or tri-alkylphenol, possibly substituted by one to four alkyl groups; or a $C_8$–$C_{30}$ alcohol, preferably $C_{10}$–$C_{22}$; or non-alkoxylated mono- or di-esters of phosphoric acid and a $C_8$–$C_{22}$ alcohol, preferably $C_{10}$–$C_{22}$.
  sulphate esters obtained from saturated or aromatic alcohols, possibly substituted by one or more alkoxylated groups (ethoxylated, propoxylated, ethopropoxylated), and for which the sulphate functions are in the form of the free acid or are partially or completely neutralised. Examples that can be cited are sulphate esters, more particularly obtained from saturated or unsaturated $C_8$–$C_{20}$ alcohols, which may contain 1 to 8 alkoxylated groups (ethoxylated, propoxylated, ethopropoxylated); sulphate esters obtained from polyalkoxylated phenol, substituted by 1 to 3 saturated or unsaturated $C_2$–$C_{30}$ hydroxycarbon-containing groups, and in which the number of alkoxylated motifs is in the range 2 to 40; sulphate esters obtained from polyalkoxylated mono-, di- or tri-styrylphenol in which the number of alkoxylated motifs is in the range 2 to 40.

It should be noted that in the case where the compounds are partially or completely in the salt form, the counter-ion can be an alkali metal such as sodium or potassium, or an ammonium ion with formula $N(R)_4^+$ where R, which may be identical or different, represents a hydrogen atom or a $C_1$–$C_4$ alkyl radical which may be substituted by an oxygen atom.

Non limiting examples of non ionic surfactants that can be cited are:
  polyalkoxylated (ethoxylated, propoxylated, ethopropoxylated) phenols substituted by at least one $C_4$–$C_{20}$ alkyl radicals, preferably $C_4$–$C_{12}$, or substituted by at least one alkylaryl radical wherein the alkyl portion is $C_1$–$C_6$. More particularly, the total number of alkoxylated motifs is in the range 2 to 100. Examples that can be cited are polyalkoxylated mono-, di- and tri-(phenylethyl) phenols or polyalkoxylated nonylphenols;

$C_6$–$C_{22}$ fatty alcohols or acids that may be polyalkoxylated (ethoxylated, propoxylated, ethopropoxylated). When present, the number of alkoxylated motifs is in the range 1 to 60. The term "ethoxylated fatty acid" includes both products obtained by ethoxylation of a fatty acid by ethylene oxide and those obtained by esterification of a fatty acid by a polyethylene glycol;

polyalkoxylated (ethoxylated, propoxylated, ethopropoxylated) triglycerides of plant or animal origin. The following are suitable: triglycerides from lard, tallow, peanut oil, butter oil, cottonseed oil, linseed oil, olive oil, palm oil, grapeseed oil, fish oil, soya oil, castor oil, rapeseed oil, coprah oil, coconut oil, and with a total number of alkoxylated motifs in the range 1 to 60. The term "ethoxylated triglyceride" encompasses both products obtained by ethoxylation of a triglyceride by ethylene oxide and those obtained by iransesterification of a triglyceride using a polyethylene glycol;

polyalkoxylated (ethoxylated, propoxylated, ethopropoxylated) sorbitan esters, more particularly esters of sorbitol cyclised with $C_{10}$ to $C_{20}$ fatty acids such as lauric acid, stearic acid or oleic acid, and with a total number of alkoxylated motifs in the range 2 to 50.

The formulations can include other additives that are conventional in this field, which may act, inter alia, as wetting agents, dispersing agents, disintegrating agents, binders, anti-clumping agents and/or stabilisers.

The quantity of these compounds can vary within a wide range and again depends on the type of formulation.

Examples of such compounds that can be mentioned are: ammonium or alkali metal salts of alkylnaphthalene sulphonates condensed with formol; ammonium or alkali metal salts of 4,4'-dihydroxybiphenylsulphonate condensed with formol; ammonium or alkali metal salts of alkylarylphosphates or alkylarylsulphates, such as polyoxyethylenated and/or polyoxypropylenated mono-, di- or tri-styrylphenols, phosphated or sulphated, neutralised or not, and mixtures thereof. It should be noted that "ammonium" represents $N(R)_4^+$ where R, which may be identical or different, represents a hydrogen atom or $C_1$–$C_4$ hydrocarbon radicals.

The following are also suitable: alkali metal or ammonium salts of polymers comprising at least one monomer selected from unsaturated $C_3$–$C_5$ acids, dibasic acids or anhydrides, possibly combined with at least one monomer selected from unsaturated linear or branched $C_4$–$C_8$ hydrocarbon radicals.

More particularly, it is possible to use polymers comprising, as monomers, maleic acid, maleic anhydride, acrylic acid, methacrylic acid, used alone or as a mixture. Said polymers can also comprise at least one monomer selected from isobutylene or diisobutylene.

This polymer can be in the form of an acid or in the form of an alkali metal or ammonium salt. Preferably, the copolymer is in the form of sodium salts. Preferably, a polymer comprising maleic acid and/or maleic anhydride combined with isobutylene and/or diisobutylene is used. The monomers alternate in the molecule. Preferably, the proportion of monomer of acid/anhydride type with respect to the hydrocarbon type monomer is 50/50.

It should be noted that the surfactants and agents that have just been cited are different from the compounds forming part of the formulation as an anti-rebound agent. The molecular weight of the former is not as high as those of the anti-rebound agent used in the invention.

Suitable examples of anti-clumping agents are ammonium or sodium phosphates, sodium carbonate or bicarbonate, sodium acetate, sodium metasilicate, magnesium, zinc or calcium sulphate, magnesium hydroxide, calcium chloride, molecular sieves, barium or calcium oxide or silica, used alone or as a mixture.

Non limiting examples of chemical stabilisers include alkaline-earth or transition metal sulphates, sodium hexametaphosphate, calcium chloride and boric anhydride, used alone or as a mixture.

The formulations can if necessary comprise one or more inert fillers such as clays, synthetic and diatomaceous silicas, calcium or magnesium silicates, titanium dioxide, aluminium, zinc or calcium oxides, calcium or magnesium carbonates, sodium, ammonium or calcium sulphates, or carbon black, used alone or as a mixture.

The quantity of filler, if used, can readily be determined by the skilled person.

The formulations of the invention are obtained using methods that are conventional in the field.

Thus in the case where the formulations are in the form of solutions, suspensions or suspo-emulsions, the constituent elements of the formulation are brought into contact, possibly in the presence of the anti-rebound agent the use of which forms the subject matter of the invention, if the latter is not used as a tank mix.

The operation is generally carried out with stirring at a temperature close to ambient temperature.

If necessary, grinding can be carried out.

It should be noted that it is possible to introduce conventional additives during preparation of the formulation, such as anti-foaming agents, selected from silicone substances, for example.

When the formulation is in powder form, a drying step is carried out after bringing the various constituent elements of the formulation into contact.

Drying takes place using conventional means. Preferably, however, said drying is by spraying, i.e., spraying a suspension into a hot atmosphere (spray-drying). This hot atmosphere is advantageously air.

Spraying can be carried out using any known spray-drier, for example a rose or other type spray nozzle. It is also possible to use turbine sprayers.

Drying can take place in a co-current or in a counter-current.

Regarding the spray techniques that can be used in the present process, particular reference should be made to the standard text on the subject by MASTERS, entitled "SPRAY DRYING" (second edition, 1976, Publisher George Godwin—London).

It should be noted that it is also possible to use the spray drying operation using a flash reactor, for example of the type described in French patent applications FR-A-2 257 326, FR-A-2 419 754 and FR-A-2 431 321.

By way of illustration, the inlet gas temperature during drying is in the range 150° C. to 250° C.

Clearly, the temperature to which the active principle is subjected during drying is lower than the degradation temperature of the constituent elements of the formulation.

Finally, if necessary, the solid formulation obtained can be formed by granulation and/or extrusion to produce granules.

EXAMPLE

This example evaluates the retraction rate of a compound present in an aqueous medium.

The rates were measured with a NAC HSV-1000 camera that could take 1000 colour images per second. The camera's resolution was 350/370 HTV lines.

When recording the images, a continuous arc lamp and/or a high power stroboscopic source was used.

The hydrophobic surface onto which the drop fell was constituted, by a square glass plate with 1 cm sides treated with stearic acid.

The table below summarises the results obtained:

| Compound | Concentration (g/l) | Retraction rate (mm/s) |
|---|---|---|
| Water | — | 900 |
| Geropon T36 (*) | 1 | 750 |
| Polyethylene glycol (MW = $5.10^6$ g/mol) | 0.5 | 50 |
| Jaguar 8000 (*) (MW~$2.10^6$ g/mol) | 1 (pH = 7) | 13.8 |
| Ethylhydroxyethyl cellulose (MW~$10^5$ g/mol) | 1 | 2 |

(*) Sold by Rhodia Chimie

What is claimed is:

1. A process for improving the anti-rebound properties of a plant protection formulation comprising water and pesticides or agents controlling plant growth, said improvement comprising the step of adding to said formulation an anti-rebound amount of at least one anti-rebound compound, wherein said anti-rebound compound has:

an elongational viscosity of twice or more that of water, and a flow viscosity of less than or equal to six times that of water, and wherein the concentration of the anti-rebound compound is of from 0.05 to 3 g/l.

2. A process according to claim 1, wherein the elongational viscosity of the compound is ten times or more that of water.

3. A process according to claim 1, wherein the flow viscosity of the compound is 3 times or less that of water.

4. A process according to claim 3, wherein the flow viscosity of the compound is 1.5 times or less that of water.

5. A process according to claim 1, wherein said compound is a hydrosoluble or hydrodispersible polymer with a molecular weight in the range $5 \times 10^4$ to $5 \times 10^6$ g/mol.

6. A process according to claim 5, wherein said molecular weight is in the range $10^6$ to $5 \times 10^6$ g/mol.

7. A process according to claim 1, wherein the retraction rate of the compound is 200 mm/s or less.

8. A process according to claim 1, wherein the compound is a polysaccharide of animal origin, a polysaccharide of vegetable origin, a polysaccharide of bacterial origin, polyvinyl alcohol, or polyphenyl alcohol.

9. A process according to claim 1, wherein the compound is a polyoxyalkyenated glycol, the alkylene oxide portion corresponding to ethylene oxide, or propylene oxide, or a mixture thereof, or a copolymer obtained from an alkylene oxide and at least one saturated or unsaturated monomer comprising:

one or more carboxyl group in the form of an acid, an alkali metal salt, an ester or an amide, an amino or nitrile group, or a heterocyclic group containing nitrogen.

10. A process according to claim 1, wherein the compound is an alkali metal, alkaline-earth metal or ammonium lignosulphonate.

11. A process according to claim 1, wherein the compound is a polymer obtained from at least one saturated or unsaturated monomer, comprising one or more carboxylic groups, in the form of an acid, alkali metal salts, ester or an amide, or containing an amino or nitrile group, or comprising a heterocyclic group containing nitrogen, or a copolymer obtained by reacting at least one of said monomers with at least one second hydrocarbon-containing monomer carrying one or more ethylenically unsaturated bonds.

12. A process according to claim 1, wherein the total concentration of the compound in the formulation is in the range 0.05 to 0.5 g/l.

13. A process according to claim 1, wherein the compound is added to the formulation during application of said formulation.

14. A process according to claim 1, wherein the compound is added to the formulation during preparation of said formulation.

* * * * *